United States Patent [19]

Koeneman

[11] Patent Number: 4,621,629

[45] Date of Patent: Nov. 11, 1986

[54] COMPRESSION HIP SCREW

[75] Inventor: James B. Koeneman, Mesa, Ariz.

[73] Assignee: Harrington Arthritis Research Center, Phoenix, Ariz.

[21] Appl. No.: 764,319

[22] Filed: Aug. 12, 1985

[51] Int. Cl.$^4$ .............................................. A61F 5/04
[52] U.S. Cl. ........................... 128/92 YS; 128/92 YE
[58] Field of Search ............ 128/92 R, 92 B, 92 BA, 128/92 BB, 92 BC

[56] References Cited

U.S. PATENT DOCUMENTS

| | | | |
|---|---|---|---|
| 2,801,631 | 8/1957 | Charnley | 128/92 BB |
| 3,051,169 | 8/1962 | Grath | 128/92 BB |
| 3,076,453 | 2/1963 | Tronzo | 128/92 BA |
| 3,641,590 | 2/1972 | Michele | 3/1 |
| 3,918,441 | 11/1975 | Getscher | 128/92 BC |
| 3,986,504 | 10/1976 | Avila | 128/92 BC |
| 4,051,559 | 10/1977 | Pifferi | 3/1.912 |
| 4,091,806 | 5/1978 | Aginsky | 128/92 BC |
| 4,095,591 | 6/1978 | Graham, Jr. et al. | 128/92 BB |
| 4,304,011 | 12/1981 | Whelan, III | 3/1.91 |
| 4,379,451 | 4/1983 | Getscher | 128/92 CA |

FOREIGN PATENT DOCUMENTS 971295  11/1982  U.S.S.R. .......................... 128/92 BA

OTHER PUBLICATIONS

J. Charnley et al, "The Treatment of Displaced Fractures of the Neck of the Femur by Compression", The Journal of Bone and Joint Surgery, Feb. 1957, vol. 39B, No. 1, pp. 45–65.

Primary Examiner—Gene Mancene
Assistant Examiner—C. W. Shedd
Attorney, Agent, or Firm—Wood, Herron & Evans

[57] ABSTRACT

A compression hip screw to aid in healing of a fracture between the neck and head of a femur includes a hollow lag screw having a threaded inner end adapted to be inserted through the neck and into the head of the femur to span the fracture therebetween, a spring assembly slidably disposed within the lag screw and attached thereto, a side plate having a barrel adapted to fit over the outer end of the lag screw and a shank section for mounting to the lateral aspect of the femur, and a compression screw insertable through the barrel and into threaded engagement with the spring assembly. The compression screw seats in a recess formed at one end of the barrel and is rotatable to move the spring assembly along its threaded shaft toward the side plate. In turn, the lag screw connected to the spring assembly is urged toward the side plate which forces the femoral head against the neck of the femur to apply a compression force at the fracture therebetween. The longitudinal axes of the compression screw and spring assembly are offset from the longitudinal axes of the lag screw and barrel, so that attempted rotation of the lag screw within the barrel causes the lag screw to follow an eccentric path and frictionally engage the interior wall of the barrel to prevent such rotation.

5 Claims, 4 Drawing Figures

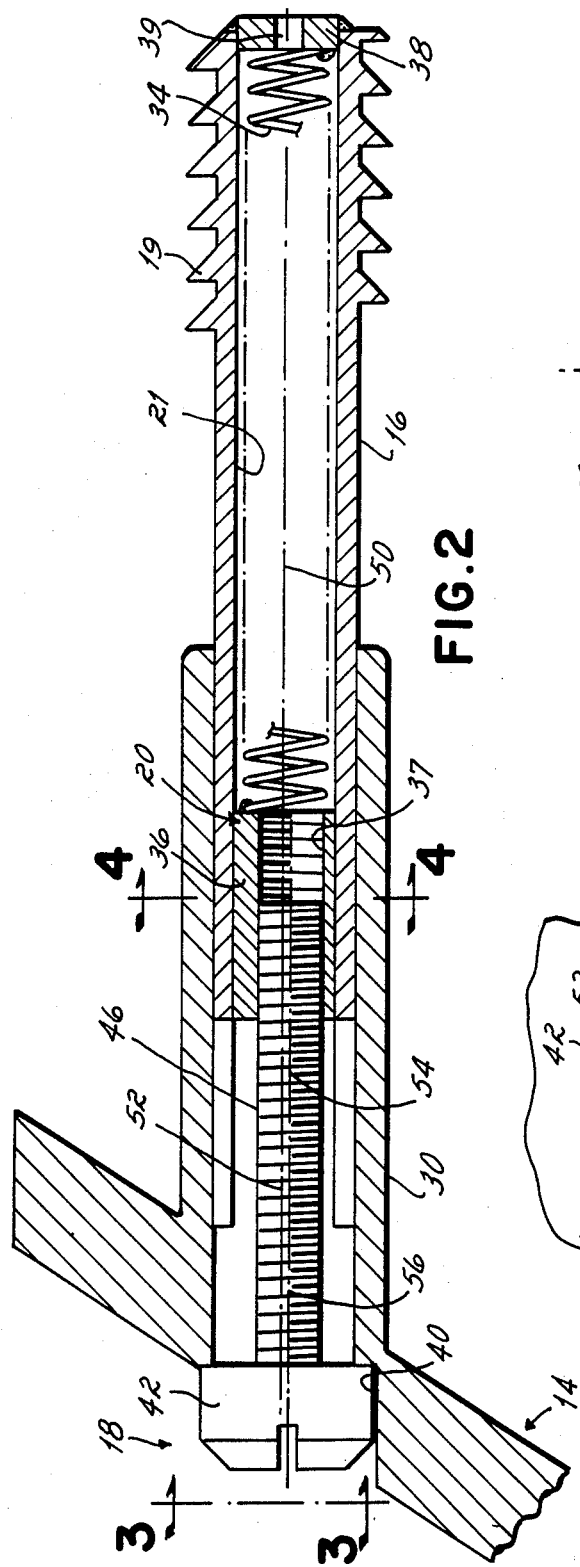
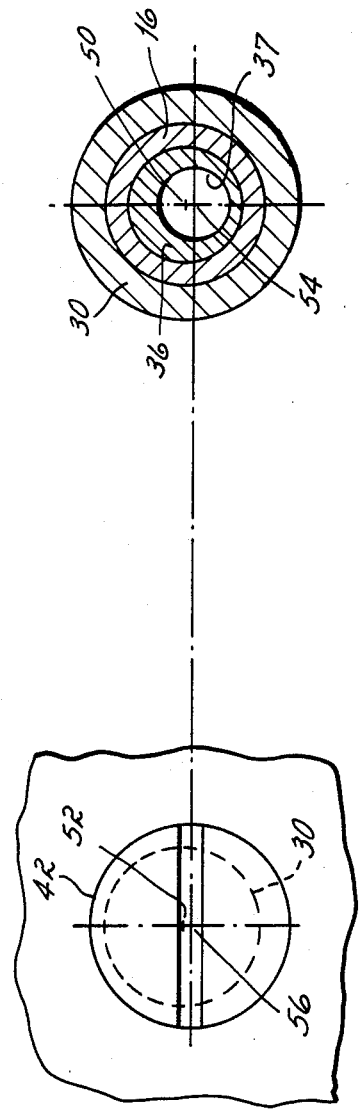
FIG. 2
FIG. 3
FIG. 4

COMPRESSION HIP SCREW

BACKGROUND OF THE INVENTION

This invention relates to devices for repairing fractures of the hip joint, and, more particularly, to a compression hip screw which applies a continuous compression force to a fracture between the head and neck of the femur.

The hip joint is one of the most heavily stressed load-carrying skeletal joints. It is essentially a ball-and-socket joint formed by the head of the femur which pivots within the cup-shaped acetabulum of the pelvis. A common problem with patients having severe arthritic conditions or osteoporosis is the occurrence of a fracture at the neck of the femur between the femoral head and its proximal end caused by an external trauma or deterioration of the bone. Unless the femoral head and neck have become so porous and weakened by osteoporosis or other conditions as to require complete replacement of the hip joint, it is preferable to reduce the fracture and induce healing.

One early surgical procedure used to repair fractures in the area of the femoral head was an autologus bone graft in which healthy bone is implanted in the area of the fracture to replace the damaged bone. A problem with this procedure is the necessity for opening a second surgical site to remove healthy bone for placement into the hip joint.

Beginning in the 1950's, compression hip screws were developed as an alternative to autologus bone grafts for the treatment of fractures at the neck and head of the femur. Early compression hip screws comprised a lag screw having external threads at one end and a threaded bore at the opposite end, a side plate formed with a shank section connected to a hollow barrel and a compression screw for connecting the lag screw to the side plate. To implant the early compression hip screws, the lag screw is first inserted through the femoral neck so that its externally threaded end enters into the dense cancellous bone of the femoral head, and the opposite, outer end extends into the neck of the femur. The next step in the surgical procedure is to mount the shank of the side plate to the lateral aspect of the femur so that the hollow barrel extends over the outer end of the lag screw. The compression screw is then inserted through the barrel and into engagement with the threaded bore of the lag screw. The head of the compression screw seats within a recess formed at the outer end of the barrel so that when tightened, the compression screw urges the lag screw toward the side plate. In turn, the femoral head is drawn by the lag screw toward the neck of the femur so that a compression force is applied to the fracture, which aids in healing. The lag screw and compression screw are axially slidable within the hollow barrel to permit movement with the femoral head if the fracture settles or the bone further deteriorates. This prevents the externally threaded end of the lag screw from piercing through the femoral head and into the cartilage of the acetabulum which could happen if the femoral head should settle to any significant degree onto the neck of the femur and the lag screw was held in a fixed axial position.

One of the problems with such early compression hip screws is that the lag screw was permitted not only to move axially within the hollow barrel but also to rotate. Rotation of the lag screw may result from walking or other activities in which load is applied to the hip joint. It was found that the lag screws of prior art hip screws could be rotated to such an extent that they would either pierce the femoral head and move into the cartilage near the acetabulum, or move in the opposite direction into the soft tissue of the leg. In either position, the lag screws were painful to the patient and required another operation to either remove or replace the entire compression hip screw.

Compression hip screws in most common use today are nearly identical to the above-described original design, except for the addition of elements to prevent rotation of the lag screw within the barrel of the side plate. Typically, the interior of the hollow barrel in conventional, modern compression hip screws is formed with a projection or key which is adapted to mate with a groove or keyway formed in the outer wall of the lag screw. The groove in the lag screw is aligned with the projection in the barrel during the surgical procedure so that when the lag screw is inserted within the barrel, the projection mates with the groove to prevent rotation of the lag screw relative to the fixed hollow barrel. Axial movement of the lag screw within the barrel is permitted, with the projection sliding along the length of the groove.

One problem with the design of modern compression hip screws is that accurate alignment must be achieved between the lag screw and side plate in order for the groove in the lag screw to align with the projection in the barrel of the side plate. As described above, the lag screw is inserted first during the surgical procedure, and thereafter the side plate is positioned so that the barrel fits over the lag screw. Preferably, the lag screw is inserted within the densest bone of the femoral head which is found near the subchondral plate at the acetabulum. If the projection in the barrel and groove in the lag screw do not align, the lag screw must be rotated to the proper position. The surgeon must be careful not to rotate the lag screw further into the femoral head if it is already near the subchondral plate because it could enter the cartilage within the acetabulum. On the other hand, if the lag screw is rotated in the opposite direction for alignment purposes it could become loosened. Often, the lag screw is either extended too deeply into the femoral head or not deeply enough in order to achieve the proper alignment between the lag screw and the barrel of the side plate.

Another important limitation of currently used compression hip screws is their inability to maintain compression at the fracture site if the fracture should settle; that is, if the femoral head settles onto the neck of the femur as the patient puts weight on the hip or as the bone deteriorates due to osteoporosis. As described above, in currently used, conventional hip screws the compression screw is inserted through the barrel of the side plate into the threaded bore of the lag screw and seats within a recess formed in the barrel of the side plate. As the compression screw is tightened, the lag screw is pulled toward the side plate and thus urges the femoral head toward the neck of the femur to apply compression at the fracture site. In order to accommodate settling of the fracture, wherein the femoral head moves toward the neck of the femur, the lag screw and compression screw are axially movable within the barrel toward the side plate. However, once the head of the compression screw is unseated from the recess in the barrel of the side plate, essentially all of the compression applied to the fracture is immediately dissipated.

Studies have shown that healing of any bone fracture is enhanced by the constant application of a compression force across the fracture, which also helps to prevent non-union of the bone while the patient is bedridden. It is common, particularly in elderly patients, for the fractured area of the femoral neck and head to collapse before it has fully healed. In order to guard against such collapse, and to lessen the likelihood of a second fracture at the same location at some future time, compression hip screws are often left in the patient permanently so long as they are not painful. Although known compression hip screws provide some additional support for the hip joint when left in place, their failure to maintain compression at the original fracture site can delay union of the bone.

One prior art compression hip screw design intended to provide a continuous compression force at the fracture site is disclosed in the article, "The Treatment of Displaced Fractures of the Neck of the Femur by Compression", by J. Charnley et al. The Charnley device comprises a lag screw which is threaded at one end for insertion into the femoral head, and also includes external threads at the opposite end. A side plate mounted to the lateral aspect of the femur is formed with a barrel which is adapted to receive the opposite, threaded end of the lag screw. The lag screw is first threaded into the femoral head, and the side plate is then secured to the lateral aspect of the femur so that the outer, threaded end of the lag screw extends within the barrel of the side plate. A compression spring is placed over the outer, threaded end of the lag screw within the barrel, and a nut is then threaded onto such outer end and into contact with the spring. By tightening the nut, the spring is compressed within the barrel, which in turn, exerts a force against the nut urging it in the opposite direction toward the side plate. Since the nut is threaded onto the lag screw, the lag screw is also urged toward the side plate by the spring.

The lag screw, and the nut threaded therealong, are axially movable within the barrel to accommodate settling of the fracture as in other prior art compression hip screws. However, in the Charnley hip screw the compression spring continues to exert a force against the nut even after axial movement of the lag screw and nut toward the side plate. While the force exerted by the compression spring is reduced as it is extended, at least some of the compression force remains upon settling of the fracture in contrast to other compression hip screws.

One problem with the Charnley compression hip screw is that the barrel of the side plate has a relatively large diameter to receive the outer end of the lag screw, and both the spring and nut which fit over the lag screw. Since the barrel extends over the outer end of the lag screw within the proximal portion of the femur, a large amount of bone must be removed in that area in order to make room for the barrel. Many surgeons are reluctant to remove large amounts of bone in patients with poor bone quality due to osteoporosis or other conditions. In addition, the Charnley device provides no means for preventing the lag screw from rotating within the barrel of the side plate. As described above, the lag screw can eventually work its way through the femoral head, or move in the opposite direction into the soft tissue of the thigh, if it is allowed to rotate within the barrel.

SUMMARY OF THE INVENTION

It is therefore among the primary objects of this invention to provide a compression hip screw for repairing fractures between the head and neck of the femur which is surgically implanted with a minimum amount of bone removed, which is adapted to apply a substantially continuous compression force to the fracture even after settling of the femoral head onto the neck of the femur, and which does not permit rotation of the lag screw relative to the barrel of the side plate.

The compression hip screw which accomplishes these objectives includes a hollow lag screw having an outer end and an inner, threaded end which is adapted to extend through the neck of the femur and into the femoral head. A side plate, having an elongate shank section connected to a hollow barrel, mounts to the lateral aspect of the femur so that the hollow barrel extends over the outer end of the lag screw. A spring assembly is slidably mounted in the interior of the lag screw adjacent its outer end, and is adapted to threadedly engage a compression screw which is insertable through the hollow barrel of the side plate. The head of the compression screw is tightened against a recess or seat formed in the hollow barrel which pulls the spring assembly, and in turn the lag screw connected thereto, toward the side plate to apply a compression force across the fracture between the femoral head and neck.

The spring assembly includes a tension spring disposed in the interior of the lag screw which is connected at one end to an inner wall of the lag screw and at the other end to a cylinder member formed with a bore having internal threads. Both the tension spring and cylinder member are slidable within the lag screw along its longitudinal axis. To apply a compression force between the femoral head and neck, the compression screw is inserted through the hollow barrel and into engagement with the internal threads in the bore of the cylinder member. The compression screw is adapted to seat within a recess formed at the barrel of the side plate so that as it is rotated, the cylinder member and tension spring are pulled toward the side plate. This causes the spring to extend so that it is placed in tension, which in turn urges the lag screw toward the side plate so as to force the femoral head against the neck of the femur in the area of the fracture with a constant compression force.

Unlike prior art compression hip screws, the spring assembly of this invention applies a continuous compression force on the lag screw even if the femoral head moves closer to the neck of the femur after the surgical procedure due to settling of the bone at the fracture site. The lag screw is slidable within the hollow barrel, but as it moves toward the side plate due to settling at the fracture site the head of the compression screw remains seated within the recess of the side plate and continues to tension the spring within the lag screw. Although the tension force applied by the spring is reduced as one end of the spring moves with the lag screw toward the side plate, the other end of the spring remains fixed to the cylinder member which is maintained in position by the compression screw. It has been found that at least half of the total initial force applied by the spring is thus retained even after substantial settling at the fracture. This ensures that continuous compression is applied to the fracture which induces faster healing, and, if the compression screw can be left in the patient, helps reduce the possibility of a postoperative fracture in the same location.

The compression hip screw of this invention also prevents rotation of the lag screw relative to the side plate. The longitudinal axis of the lag screw aligns with the longitudinal axis of the barrel formed in the side plate. However, the longitudinal axis of the threaded bore formed in the cylinder member of the spring assembly is offset from the longitudinal axis of the lag screw, and, therefore, from the longitudinal axis of the barrel. Due to this offset relationship, when the compression screw is threaded into the cylinder member its center of rotation is offset from the center of rotation of the lag screw. Rotation of the lag screw within the barrel is prevented by engagement of the lag screw with the barrel and by engagement of the head of the compression screw with the recess formed in the side plate. As the lag screw starts to rotate, it causes the compression screw to attempt to rotate. Since the axis of rotation of the compression screw is offset from the axis of rotation of the lag screw, the compression screw follows an eccentric path. Instead of rotating, the compression screw is urged against the recess in the plate. In turn, the lag screw is forced against the barrel of the side plate. The frictional engagement between the lag screw and barrel, and between the head of the compression screw and the recess in the side plate, prevents further rotation of the lag screw relative to the side plate. As described above, it is important to maintain the lag screw fixed since it is positioned near the edge of the femoral head and could work its way into the cartilage of the acetabulum if allowed to rotate.

The compression hip screw of this invention aids significantly in the healing of fractures by applying a continuous compression force across the head and neck of the femur even after settling of the fracture. Although this general problem with prior art compression hip screws is recognized in the Charnley hip screw, that design requires the removal of a great deal of bone and fails to prevent the lag screw from rotating and thus axially moving within the barrel of the side plate. By placing the spring inside of a hollow lag screw in this invention, the barrel of the side plate may be made much smaller than in the Charnley design so that much less bone must be removed. In addition, the offset relationship between the compression screw, and the barrel and lag screw, prevents rotation of the lag screw relative to the side plate.

DESCRIPTION OF THE DRAWINGS

The structure, operation and advantages of this invention will become further apparent upon consideration of the following description taken in conjunction with accompanying drawings, wherein:

FIG. 2 is an enlarged side view in partial cross section of the compression hip screw;

FIG. 3 is a partial end view taken generally along line 3—3 of FIG. 2 showing the head of the compression screw and recess in the side plate; and FIG. 4 is a partial cross sectional view taken generally along line 4—4 of FIG. 2.

DETAILED DESCRIPTION OF THE INVENTION

Figure 1:
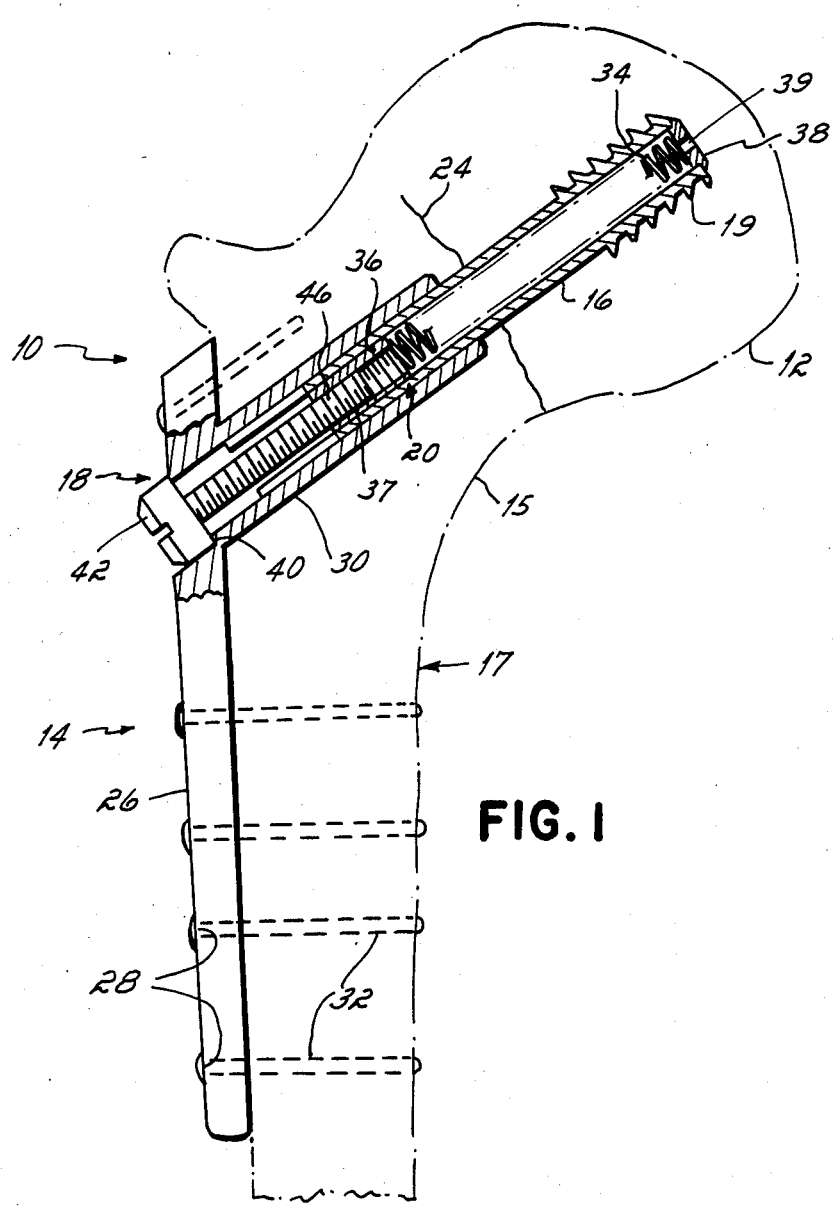
FIG. 1 is a side view in partial cross section of the compression hip screw of this invention shown implanted within a hip joint.

Referring now to FIG. 1, the compression hip screw 10 of this invention is shown mounted in place between the head 12 and neck 15 of a femur 17. The hip screw 10 comprises a side plate 14, a lag screw 16, a compression screw 18 and a spring assembly 20.

The lag screw 16 is hollow and includes external threads 19 formed at one end. The opposite end of the lag screw 16 is conventionally formed with a slot (not shown) adapted to engage a tool for turning the lag screw 16 into the femur 17. The lag screw 16 is threaded through the neck 15 of the femur 17 and seats within the dense cortical bone near the top of the femoral head 12. Preferably, the lag screw 16 extends along or at least parallel to the longitudinal axis of the femoral head and neck 12, 15 when in place within the femur 17, and spans a fracture 24 therebetween which is shown as a jagged line in the drawings for purposes of illustration.

The side plate 14 of hip screw 10 comprises a shank section 26, formed with a plurality of spaced openings 28, which is connected at one end to a hollow barrel 30. A seat or recess 40 is formed in side plate 14 at the outer end of barrel 30. The shank section 26 is adapted to mount to the lateral aspect of the femur 17 using conventional surgical nails or bone screws 32 which extend through the openings 28 into the femur 17. The barrel 30 is disposed at an angle relative to shank section 26 such that when the side plate 14 is mounted to the femur 17 the barrel 30 receives the slotted, outer end of the lag screw 16.

The spring assembly 20 functions to urge the lag screw 16, and femoral head 12 attached thereto, toward the side plate 14 to apply a compressive force to the fracture 24 and promote healing. The spring assembly 20 comprises a tension spring 34 disposed within the hollow interior of the lag screw 16 and attached at one end to the inner end 38 of the lag screw 16. The opposite end of the spring 34 is attached to one end of a cylinder member 36 which is slidable within the lag screw 16. The cylinder member 36 is formed with a bore 37 having internal threads.

The compression screw 18, having a fillister head 42 and a threaded shaft 44 is inserted through the barrel 30 and into threaded engagement with the bore 37 of cylinder member 36. The head 42 of compression screw 18 is adapted to seat within the recess 40 so that when the screw 18 is rotated it pulls the cylinder member 36 toward side plate 14 thereby extending the spring 34. This tensions the spring 34 and urges lag screw 16, attached thereto, toward the side plate 14 to apply a compression force between the femoral head 12 and neck 15 at the fracture 24.

The compression hip screw 10 of this invention provides several advantages over prior art designs which are best understood by considering a complete installation procedure. Conventionally, a wire (not shown) is first inserted through the femoral neck 15 and partially into the head 12, preferably coincident with their longitudinal axes, to define a path for insertion of lag screw 16. The inner end 38 of lag screw 16 is formed with an opening 39 which is adapted to receive the wire to help guide the lag screw 16 into the proper position within the femoral neck 15 and head 12. A standard tool is utilized to engage a slot (not shown) formed in the opposite, outer end of the lag screw 16 and thread the lag screw 16 through the femoral neck 15 and at least partially into the femoral head 12. Before the lag screw 16 is advanced to its permanent position, the side plate 14 is mounted to the femur 17 so that the lag screw 16 is received within barrel 30. The barrel 30 extends into the femoral neck 15, but is relatively small in diameter so as to minimize the amount of bone which must be removed from the femoral neck 15 in order to receive the barrel 30.

At this point in the installation procedure, the lag screw 16 is permitted to rotate within barrel 30. This feature of the instant invention makes installation much easier because the lag screw 16 need not be placed in its permanent position before the side plate 14 is mounted to the femur 17 and the barrel 30 extends over the lag screw 16. Preferably, the lag screw 16 is advanced into the femoral head 12 until its outer end extends approximately midway along the barrel 30. Lag screws 16 of differing lengths are provided so that the surgeon may choose the appropriate length for a femur 17 having given head and neck dimensions. By placing the lag screw 16 midway within the barrel 30, any cocking or tilting of the femoral head 12 relative to the neck 15 which may occur as the fracture 24 settles does not prevent movement of the lag screw 16 within barrel 30.

After the lag screw 16 is advanced to its permanent position with the side plate 14 in place, the compression screw 18 is then inserted through the barrel 30 and into threaded engagement within the bore 38 of cylinder member 36. The compression screw 18 is turned until its head 42 seats within the recess 40 formed in side plate 14. Thereafter, further turning of compression screw 18 causes the cylinder member 36 to slide within lag screw 16 toward the side plate 14. In turn, the spring 34 attached to the cylinder member 36 is extended or placed in tension. The lag screw 16, attached to spring 34, is thus urged toward the side plate 14 under the tension force applied by spring 34. In response to the force applied to lag screw 16, the femoral head 12 is urged toward the neck 15 of the femur 17 at the fracture 24. This applies a compression force across the fracture 24 to aid in healing.

Importantly, the compression force applied across fracture 24 is not completely dissipated as the fracture 24 settles when the patient begins to move about and apply weight on the femur 12 or as the bone deteriorates further. As the fracture 24 settles, the femoral head 12 and lag screw 16 move toward the neck 15 of the femur 17. The lag screw 16 slides within the barrel 30, but the cylinder member 36 remains in a fixed position because it is slidable within the lag screw 16. Some tension is relieved from the spring 34 as its end connected to the lag screw 16 moves axially with the lag screw 16 toward the side plate 14. However, the compression screw 18 is initially tightened to such an extent that normal settling of the fracture 24 will only reduce the compression force applied by the spring 34 at the fracture 24 by about one half. Therefore, continuous compression urges the femoral neck 15 and head 12 together even after normal settling of the fracture 24. This greatly enhances healing of the fracture 24, and, if the hip screw 10 may be left in place after the operation, helps to prevent future fractures at the same location.

As mentioned above, it is important to prevent rotation of the lag screw 16 relative to side plate 14 once the hip screw 10 is properly positioned. Although rotation of lag screw 16 within barrel 30 is permitted during the installation procedure, the lag screw 16 is prevented from rotating once the compression screw 18 is in place. This is due to the eccentricity of the connection between the cylinder member 36 and compression screw 18, and the lag screw 16.

As best shown in FIGS. 2-4, the longitudinal axis 50 of lag screw 16 aligns with the longitudinal axis 52 of barrel 30. However, the longitudinal axis 54 of the bore 38 in cylinder member 36 is offset from the longitudinal axes 50, 52 of lag screw 16 and barrel 30, respectively, and aligns with the axis 56 of the shaft 46 of compression screw 18. Therefore, the center of rotation of compression screw 18 is offset or eccentric with respect to the center of rotation of lag screw 16. During the installation operation, the compression screw 18 is permitted to freely rotate within the recess 40 formed in side plate 14 because it directly aligns with the bore 37 in cylinder member 36 and the cylinder member 36 is axially slidable within lag screw 16. But once the compression screw 18 is seated within the recess 40 of barrel 30, rotation of lag screw 16 is resisted. This resistance to rotation is created by the frictional engagement between the lag screw 16 and barrel 30, and between the head 42 of compression screw 18 and its seat 40 in the side plate 14. As applied forces tend to rotate the lag screw 16, its connection through the spring assembly 20 to the eccentrically disposed compression spring 18 causes the lag screw 16 to rotate in an eccentric path. Since the longitudinal axis 50 of lag screw 16 aligns with the longitudinal axis 52 of barrel 30, eccentric rotation of lag screw 16 causes it to frictionally engage the sides of barrel 30.

In a presently preferred embodiment of this invention, the seat 40 for the head 42 of compression screw 18 is formed to permit alignment of its shaft 46 with the bore 37 of cylinder member 36 in only one position, as shown in FIG. 2. Once the head 42 is seated in the aligned position, the compression screw 18 is prevented from rotating in an eccentric path because of frictional engagement between its head 42 and the seat 40. If forces applied to the lag screw 16 begin to rotate the compression screw 18, through its connection to spring assembly 20, the head 42 of the compression screw 18 is urged along an eccentric path and engages the sides of the recess 40 to prevent such rotation.

The eccentric relationship between the lag screw 16 and barrel 30, relative to the compression screw 18 and spring assembly 20, therefore creates frictional engagement between the lag screw 16 and barrel 30 and/or the head 42 of compression screw 18 and the recess 40 in side plate 14. This effectively prevents the lag screw 16 from rotating and working free as a patient moves about and applies weight to the femur 12, which could result in axial movement of the lag screw 16 through the femoral head 12 or in the opposite direction to the thigh.

While the invention has been described with reference to a preferred embodiment, it will be understood by those skilled in the art that various changes may be made and equivalents may be substituted for elements thereof without departing from the scope of the invention. In addition, many modifications may be made to adapt to a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

Wherefore I claim:

1. A compression screw for repairing a fracture between the head and neck of a femur, comprising:
   a hollow lag screw having an outer end and an externally threaded inner end, said threaded inner end being adapted to be inserted through the neck and into the head of the femur, said lag screw spanning the fracture between the femoral head and neck;
   a spring assembly slidably disposed within said hollow lag screw, said spring assembly having an inner end attached to said inner end of said hollow lag screw;
   a side plate having a shank section connected to a barrel, said shank section being adapted to mount to the femur so that said barrel extends over said outer end of said hollow lag screw;
   a compression screw extending through said barrel and into engagement with said spring assembly, said compression screw being adapted to urge said spring assembly and said lag screw attached thereto toward said side plate, the femoral head being urged by said lag screw against the neck of the femur thereby applying a compression force at the fracture therebetween.

2. The compression hip screw of claim 1 in which said spring assembly comprises a tension spring and a cylinder member formed with a threaded bore, said tension spring being attached at said inner end to said lag screw and at the other end to said cylinder member, said compression screw being adapted to be threaded into said threaded bore of said cylinder member and rotated for urging said cylinder member and tension spring toward said side plate to apply tension to said tension spring.

3. The compression hip screw of claim 1 in which said compression screw includes a threaded shaft and a head, said side plate being formed with a recess at the connection of said barrel to said shank section, said recess being adapted to receive said head of said compression screw.

4. A compression hip screw for repairing a fracture between the head and neck of a femur, comprising:
   a hollow lag screw having an outer end, an externally threaded inner end and a longitudinal axis, said inner threaded end being adapted to be inserted through the neck and into the head of the femur, said lag screw spanning the fracture between the femoral neck and head;
   a spring assembly including a tension spring and a cylinder member slidably disposed within said hollow lag screw, one end of said tension spring being connected to said lag screw and the other end of said tension spring being connected to said cylinder member, said cylinder member being formed with a threaded bore having a longitudinal axis;
   a side plate including a shank section connected to a barrel having a longitudinal axis, said side plate being formed with a recess at said connection between said shank section and said barrel, said shank section being adapted to mount to the femur so that said barrel extends over said outer end of said hollow lag screw; and
   a compression screw including a head and a threaded shaft having a longitudinal axis, said compression screw being inserted through said barrel so that said threaded shaft engages said threaded bore of said cylinder member and said head seats within said recess, said compression screw being rotatable relative to said side plate to move said cylinder member along said threaded shaft thereof toward said side plate thereby tensioning said tension spring, said tension spring urging said lag screw toward said side plate so that the femoral head is forced against the neck of the femur thereby applying a compression force at the fracture therebetween.

5. The compression hip screw of claim 4 in which said longitudinal axis of said lag screw aligns with said longitudinal axis of said hollow barrel, and said longitudinal axis of said threaded shaft of said compression screw aligns with said longitudinal axis of said bore in said cylinder member, said longitudinal axes of said compression screw and said bore in said cylinder member being offset from said longitudinal axes of said lag screw and said barrel, said lag screw being urged to rotate in an eccentric path relative to said longitudinal axis of said hollow barrel and thereby frictionally engage said hollow barrel to prevent rotation thereof due to said offset position of said axes of said lag screw and said hollow barrel relative to said axes of said compression screw and said bore of said cylinder member.

* * * * *